US006949066B2

(12) United States Patent
Bearnson et al.

(10) Patent No.: US 6,949,066 B2
(45) Date of Patent: Sep. 27, 2005

(54) ROTARY BLOOD PUMP DIAGNOSTICS AND CARDIAC OUTPUT CONTROLLER

(75) Inventors: Gill Bearnson, Salt Lake City, UT (US); Gordon B. Jacobs, Salt Lake City, UT (US)

(73) Assignee: World Heart Corporation, Oakland, CA (US)

( * ) Notice: Subject to any disclaimer, the term of this patent is extended or adjusted under 35 U.S.C. 154(b) by 263 days.

(21) Appl. No.: 10/225,906

(22) Filed: Aug. 21, 2002

(65) Prior Publication Data

US 2004/0039243 A1 Feb. 26, 2004

(51) Int. Cl.[7] .................... A61N 1/362
(52) U.S. Cl. .................... 600/16
(58) Field of Search .................... 600/16–18

(56) References Cited

U.S. PATENT DOCUMENTS

| | | | | |
|---|---|---|---|---|
| 5,326,344 | A | 7/1994 | Bramm et al. | 623/3 |
| 5,385,581 | A | 1/1995 | Bramm et al. | 623/3 |
| 5,888,242 | A | 3/1999 | Antaki et al. | 623/3.28 |
| 5,928,131 | A | 7/1999 | Prem | 600/16 |
| 6,066,086 | A | 5/2000 | Antaki et al. | 600/17 |
| 6,080,133 | A | 6/2000 | Wampler | 604/131 |
| 6,129,660 | A | 10/2000 | Nakazeki et al. | 600/17 |
| 6,135,943 | A | 10/2000 | Yu et al. | 600/16 |
| 6,183,412 | B1 | 2/2001 | Benkowski et al. | 600/16 |
| 6,264,601 | B1 | 7/2001 | Jassawalla et al. | 600/16 |
| 6,293,901 | B1 | 9/2001 | Prem | 600/17 |
| 6,375,607 | B1 | 4/2002 | Prem | 600/17 |
| 2005/0004418 | A1 * | 1/2005 | Morello | 600/16 |

* cited by examiner

*Primary Examiner*—Scott M. Getzow
(74) *Attorney, Agent, or Firm*—Holland & Hart LLP

(57) ABSTRACT

A method and apparatus for controlling a ventricular assist device are disclosed. The method includes the step of providing a ventricular assist device which can be defined in terms of operational parameters such as pump speed or current. Measuring at least one physiological parameter reflecting a physiological state corresponding to a patient. Correlating at least one physiological parameter measured from the patient to at least one operational parameter using an estimation method. Selecting a physiological state definable by desired values of the physiological parameters. Monitoring at least one operational parameter. Controlling input values of the operational parameter based on output from the monitoring step. The apparatus includes a pump driven by a motive drive and having an impeller. A sensor detects the value of an operational parameter of the pump. A processor provides a statistical correlation between patients physiological parameter and the operational parameter of the pump and adjusts the operational parameter to affect a predetermined optimal physiological state.

47 Claims, 10 Drawing Sheets

150
Set Nominal State 152
Set Motor Control 154
Monitor 156
Motor Parameters 158
Physiological Parameters 160
166
Correlate Physiological Parameters to Motor Parameters
$Q = w^T \Theta$ 162
164
Test For Adequacy ?
No
Yes
Output Model Parameters 168

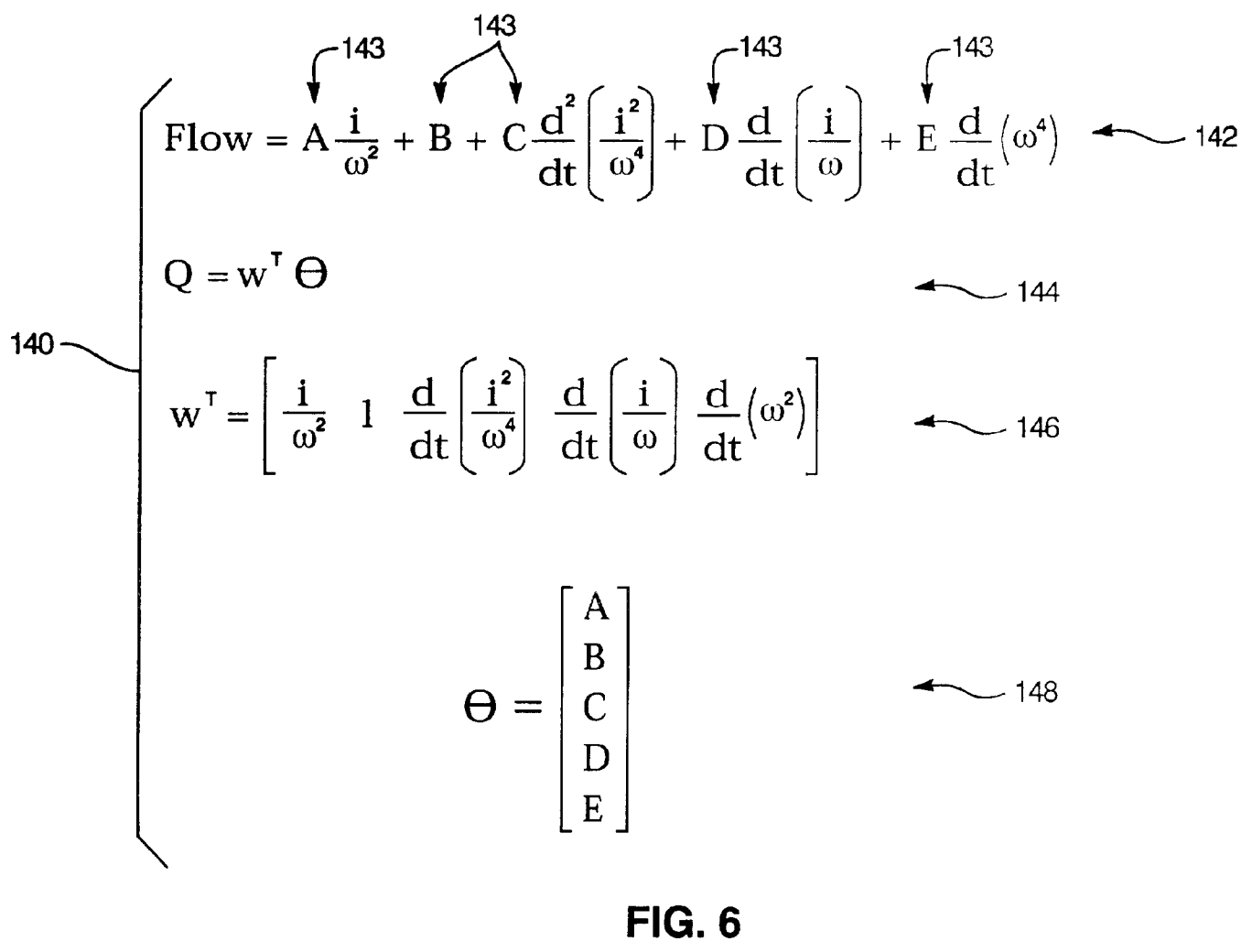

$$\text{Flow} = A\frac{i}{\omega^2} + B + C\frac{d^2}{dt}\left(\frac{i^2}{\omega^4}\right) + D\frac{d}{dt}\left(\frac{i}{\omega}\right) + E\frac{d}{dt}\left(\omega^4\right)$$

$$Q = w^T\Theta$$

$$w^T = \begin{bmatrix} \frac{i}{\omega^2} & 1 & \frac{d}{dt}\left(\frac{i^2}{\omega^4}\right) & \frac{d}{dt}\left(\frac{i}{\omega}\right) & \frac{d}{dt}\left(\omega^2\right) \end{bmatrix}$$

$$\Theta = \begin{bmatrix} A \\ B \\ C \\ D \\ E \end{bmatrix}$$

FIG. 6

ROTARY BLOOD PUMP DIAGNOSTICS AND CARDIAC OUTPUT CONTROLLER

THE FIELD OF THE INVENTION

This invention relates to a pump controller and method of operating same. More particularly, the invention relates to a rotary blood pump controller and method for real time control of the pump to give optimum performance to the patient benefitting from the pump and to give diagnostic feed back to those monitoring the patient.

BACKGROUND

The invention described here is related to the clinical use and automatic control of a blood pump in the human circulation system. In general there are various physiological parameters that are of interest to clinicians that care for patients that are undergoing circulatory assistance from a mechanical device. Many of these same parameters may be desirable to be obtained for use in an automatic cardiac output controller to be used in combination with the mechanical pump. Examples of physiological parameters that could be used include flow through the pump and pressures at the inflow and the outflow of the pump.

One method to obtain a flow rate through a blood pump is to place sensors directly in the flow path. However this approach is saddled with reliability issues of sensors directly exposed to blood, in addition to wires and cable associated with such sensors. Sensor placement directly in the blood flow is undesirable because the blood can cause malfunction of the sensor due to contamination of the sensing element and wiring, or due to blood clotting around the sensing element resulting in lost sensitivity of the sensor. The sensor itself can also damage the blood cells themselves creating blood clots.

Some physiological controllers may rely on measuring pressure to determine desired physiological parameters. However, these sensors are difficult to implement within a patient, lack the required sensitivity, and are quite expensive.

Some physiological controllers adjust the speed of the pump based upon a comparison to failure levels of the patient's heart. U.S. Pat. Nos. 5,888,242 and 6,066,086 to Antaki et al. teach an automatic speed control system which continually adjusts the speed of an implanted cardiac assist blood pump to an optimum level for the varying physiological needs of the patient. It does this by periodically iteratively incrementing the speed set point of the pump. When the system detects the imminence of a ventricular collapse at the end of systole, it decrements the speed set point by a predetermined safety margin. These attempts at avoiding the direct sensor placement in the blood suffer some drawbacks. For example, a speed set point of the heart pump that is set at a predetermined point compared to ventricular collapse may not be the optimum speed for a particular patient. Additionally, incrementing the speed set point of a heart pump toward an imminent ventricular collapse comparison point may be dangerous.

Additionally, choosing the speed set point of a heart pump by arbitrarily setting the speed a predetermined amount away from a failure point does not provide any diagnostic feedback to the physician monitoring the patient.

Thus, it would be an advancement in the art to provide a physiological heart pump or cardiac output controller that did not need blood flow sensors for daily operation. It would be an additional advancement in the art to provide such a cardiac output controller that better tracked the optimum pump performance based on the patient's physiological makeup. It would be a further advancement in the art if the cardiac output controller were more cost-effective. It would be yet another advancement in the art if the cardiac output controller could provide diagnostic feedback.

Such a cardiac output controller, and method of operating same, in accordance with the present invention is disclosed and claimed herein.

BRIEF SUMMARY OF THE INVENTION

The apparatus of the present invention has been developed in response to the present state of the art, and in particular, in response to the problems and needs in the art that have not yet been fully solved by currently available blood pump controllers. The present invention solves many or all of the foregoing problems by introducing a system and method which uses statistical estimation techniques to correlate heart pump operational parameters to a patient's physiological parameters to provide diagnostics in a rotary blood pump.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 6 is a chart illustrating one embodiment of a fitted equation containing coefficients and various terms on which flow rate may be found to depend or correlate in accordance with the invention;

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 10, is not intended to limit the scope of the invention, as claimed, but is merely representative of the presently preferred embodiments of the invention.

The presently preferred embodiments of the invention will be best understood by reference to the drawings, wherein like parts are designated by like numerals throughout.

Figure 1:
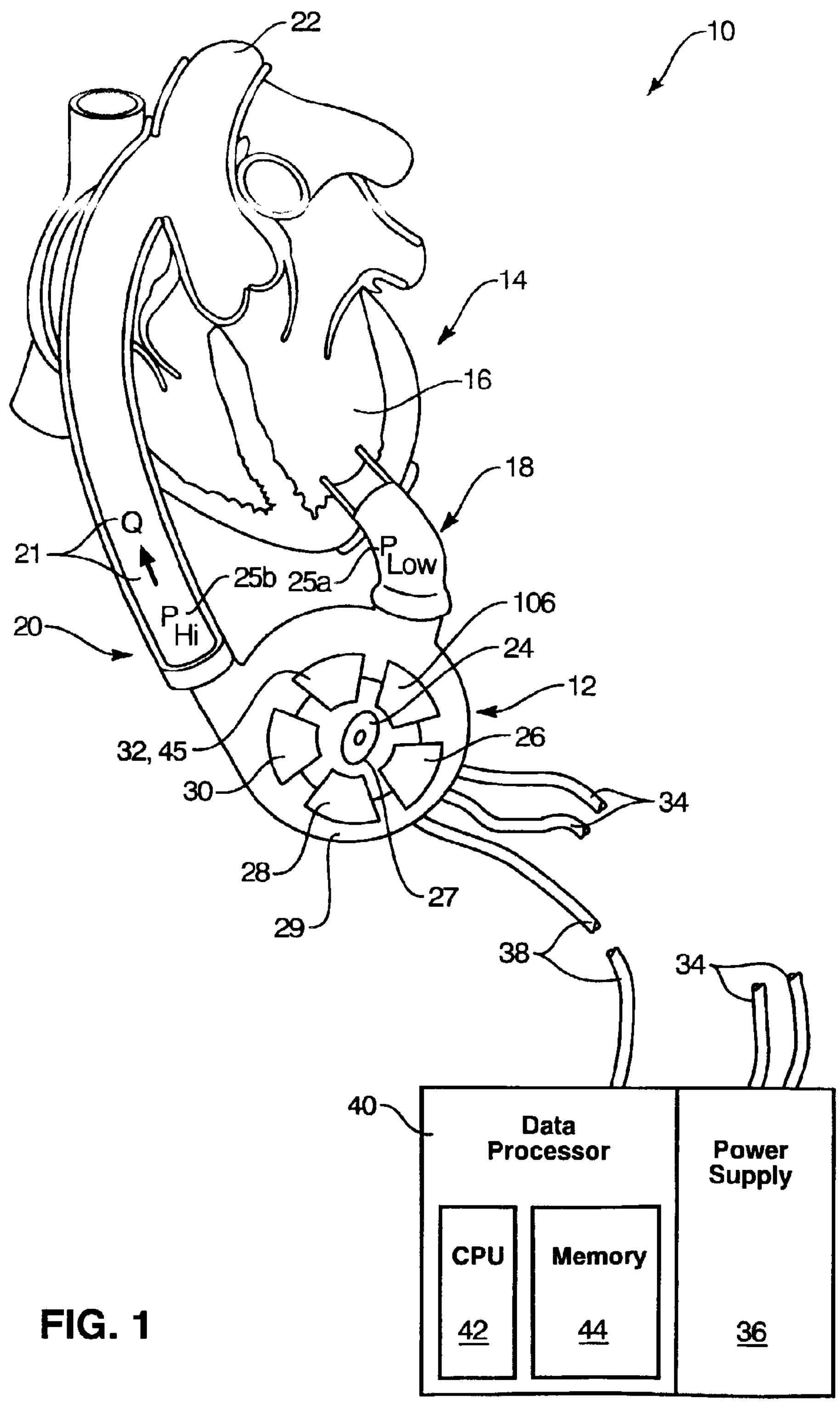
FIG. 1 is a schematic block diagram of an implemented system in accordance with the invention.

Referring to FIG. 1, a system 10 operates to provide an effective assistance to a failed ventricular portion of a heart. In general, such a system 10 may include a ventricular assist device 12 (VAD 12) operably connected to a native heart 14 of a patient. Typically, a native ventricle 16 has been damaged such that blood flow is limited, and reliability is inadequate to assure consistently healthy living of the patient.

The damaged or inadequately functioning native ventricle 16 may have been subjected to an infarction, traumatic injury, or the like. Accordingly, inadequate operability may include reduced volumetric flow, inadequate pressure rise, inadequate volumetric stroke of the ventricle, inadequate duration of the stroke, inadequate frequency of the stroke, or the like. A native ventricle 16 may be connected to an assist inlet 18 corresponding to the ventricular assist device 12. Typically, an assist outlet 20 of the ventricular assist device 12 provides a blood flow to or toward an aorta 22 thereby assisting the native heart 14.

The ventricular assist device 12 may include an impeller 24. In certain embodiments, the impeller 24 may be a rotary impeller sweeping through a volumetric chamber 27 in order to drive blood to an increased pressure and flow at the assist outlet 20. In alternative embodiments, such as in those situations where a clinical system 10 includes a ventricular assist device 12 exterior to the body, or other types of rotary pumps. The impeller 24 may be driven by an affirmatively connected shaft or other connector to a motive drive 26, such as a motor 26. However, in certain embodiments, in order to provide additional blood flow around the impeller 24, and to prevent occurrences of stagnant flow, blood shear, or other conditions which cause cellular damage, thrombosis or platelet release, the impeller 24 may be magnetically levitated to suspend within an imposed magnetic field. Accordingly, the magnetic field strength, the power drawn by the maintenance of the magnetic field, and other factors may provide characteristics of the impeller 24. Similarly, electrical voltage, electrical current, angular speed and the like may characterize a motor drive 26 or other motive means 26 for the impeller 24. Similarly, a pressure differential may exist between the assist inlet 18 and the assist outlet 20. Correspondingly, a pressure differential exists between the assist outlet 20, and the assist inlet 18, by virtue of the vascular resistance to flow, reflecting the physiological condition or state of the patient. For example, during exercise, additional demand for blood, may cause variations in vascular pressures and dilations. Muscular contractions may also provide periodic or sustained variations in vascular dilation and back pressure felt at the assist outlet 20. The release of hormones such as adrenalin, may also affect the contractibility of the heart, or dilate vessels providing increased area and decreased resistance to flow.

In general, a motive drive 26 may connect to an impeller 24 within a chamber 27 to constitute a pump 106. Physical configuration of the pump may be modified according to a host of factors including physiological compatibility, available area, desired flow patterns and speeds, the smoothness of transitions between various conduit regions in order to minimize shear flows and subsequent or consequent blood cell damage, and the like. Thus, the schematics of FIG. 1 merely demonstrate the concept that some type of motive drive 26, such as an electric motor, an electromagnetic field generation system, or the like, may be used to drive an impeller 24 in order to move blood flow and increase blood pressure at an assist outlet 20. In certain embodiments, the motive drive 26 may be embedded within a wall of a chamber 27, and completely isolated from the impeller 24, in order that the impeller 24 should not provide any recesses that might generate blood clots to damage other portions of the body.

In certain embodiments, a power control 28 may control the motor 26. In general, a power control 28 may be thought of as simply a system controller 28. The system controller 28 may control speed, frequency, electrical current, electrical voltage, or various other parameters that may be used to control operation of a motive drive 26 or pump 106. The controller 28 may be configured to provide "open-loop" control in which the motor 26 operates independently from physiological parameters, or feedback thereof. In other embodiments, the system controller 28 may receive control, or provide control that incorporates either biological and physiological parameter feedback, or other types of "closed-loop" control for the motive drive 26. In one embodiment, the system controller 28 may control the motive drive 26 in accordance with operational parameters of the motive drive 26, that have been correlated with, or correspond to actual physiological parameters of interest to a doctor and patient by statistical methods.

Statistical methods of control are not the only correlating methods. Deterministic methods may also be used. Nevertheless, in general, it has been found with respect to various embodiments of apparatus and methods in accordance with the present invention, that modeling or curve fitting a relationship between operational parameters of the motive drive 26 or the pump 106, and physiological parameters of the native heart 14, its constituent parts, such as the native ventricle 16 and aorta 22, and the general cardiovascular system of a patient, provide an excellent mechanism for control. That is, correlating by either statistical or other approximation techniques or mathematical relationship techniques, the operational parameters of the motive drive 26, to the physiological parameters of interest to a doctor and patient, and corresponding to the native heart 14 and its corresponding vascular system provide direct feedback control of the operation of the motive drive 26, in terms of the inherent operational parameters of the motive drive 26, as a surrogate for other correlated physiological parameters of interest.

A major benefit of providing feedback control to the motive driver 26, based on operational parameters of the motive driver, is that it is the ventricular assistance 12 does not require invasive physiological measuring devices on an ongoing basis to determine optimal operation of the ventricular assistance 12. Further, the present invention avoids sensors in the blood flow which may become a source for infection, blood clotting, blood cell damage, which may damage the integrity of a measurement, and create unreliability due to biological influences on otherwise mechanical and electrical devices. Not only does the biological protection scheme of a human body tend to alter the physical condition and performance of mechanical and electrical devices, but the presence of mechanical and electrical devices tends to affect biological processes. In general, the system or controller 28 may be embedded in a motive drive 26, or may be embedded in a processor 30, or may be a separate mechanism. The processor 30 may also be embedded in the system controller 28, or in the motive driver 26, or may be completely external thereto. In certain embodiments, the processor 30 may receive signals from an operational parameter sensor 32, in order to determine a set point or control signal for the system controller 28, to operate the motive driver 26. In certain embodiments, a processor 30 may even be external to the ventricular assist device 12, and external to the body. For example, in a clinical setting, the ventricular assist device 12 may operate externally to the body for some period of time. In practice, for an individual attempting to return to substantially normal life, a ventricular assist device 12 may be embedded within the body, and the processor 30 and sensors 32 are then most likely to be incorporated in an integrated system 10 that fits substantially entirely within the body.

The processor 30 is responsible for processing inputs received from a sensor 32, which inputs reflect a condition of the motive drive 26, the impeller 24, or other operational parameters. In general, the sensors 32 may also include biological sensors 45 monitoring biological processes. However, in certain embodiments, the sensors 32 in operation may be exclusively dedicated to sensing parameters correspondent to the motive drive 26, the impeller 24, or the like. Thus, the sensors 32 provide the mechanical, electrical, or both types of feedback information on the operation of the motive driver 26. Those inputs may be correlated prior to regular operation against the physiological parameters of interest. Thus, in operation, the sensors 32 need only assess the operation of the motive drive 26, impeller 24, and the like, as a correlated reflection of physiological parameters. The sensors 32 in such an embodiment may be embedded in a system integrating a processor 30 with a controller 28, in order to provide control to a motive drive 26.

Power lines 34 will typically require substantial power inputs from an external power supply 36. Complete integration of a power supply 36 into a system 10 completely embedded within a body, will typically require a recharging mechanism depending on electromagnetics. That is, a non-invasive recharging system would typically require some type of electromagnetic coupling for recharging of a battery, or the like. Otherwise, the sustained power requirements for blood flow corresponding to a ventricular assist device 12, will demand that an external power supply 36 provide power lines through a percutaneous cable in order to reach the motive drive 26 and provide power thereto.

Similarly, data lines 38 may provide information to and from the ventricular assist device 12 to a remote data processor 40. As computer systems have become miniaturized, and as the processor 30 may be dedicated strictly to the control of the motive driver 26, or providing signals to a controller 28 responsible therefor, the data lines 38 may be used only for calibration or diagnostic work in a clinical setting. Thus, the data lines 38 to a remote data processor 40 may be advantageous for high speed or high volume data processing during calibration of a ventricular assist device 12 to the operation of a particular patient.

The impracticality of an individual carrying a data processor 40 external to the ventricular assist device 12, where the operation thereof is so dependent on the proper processing of data, may prohibit the use of a remote data processor 40 except in a very controlled clinical setting. Meanwhile, the newly miniaturized computerized control mechanisms of modern science, tend to militate for integration of the sensors 32, processor 30, controller 28, and motive driver 26 all within the housing 29 or the walls thereof, which support the impeller 24. In general, data processor 40 may be any suitable type of computer, typically including a central processing unit 42 (CPU) and a memory device 44.

Figure 2:
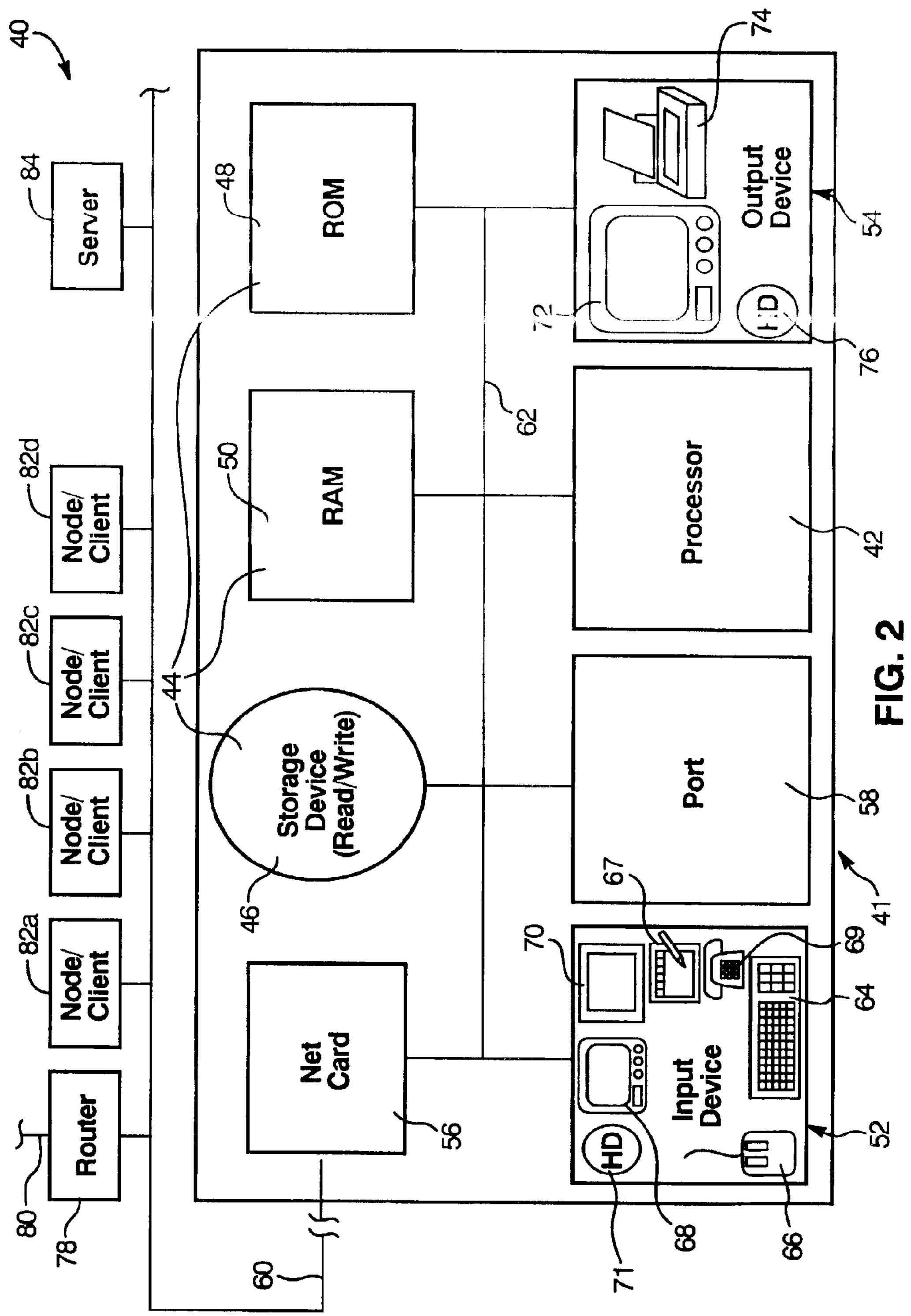
FIG. 2 is a schematic block diagram of a generic, general purpose digital computer such as may be used in various portions of an apparatus and method in accordance with the invention.

Referring to FIG. 2, the processor 30, the data processor 40, and other devices capable of computation may be represented as the system 40. That is, minimal or maximal processing capability may be provided for the processor 30, the data processor 40, or the like. Thus, in general, it is instructive to consider that various capabilities, devices, functionalities, peripheral devices, and the like that may be either embedded as part of, or connected as related devices, to the processor 30, or the data processor 40. The processor 40 may implement the invention on one or more nodes 41, (client 41, computer 41) containing a processor 42 (CPU 42). All components may exist in a single node 41 or may exist in multiple nodes 41, 82 remote from one another. The CPU 42 may be operably connected to a memory device 44. A memory device 44 may include one or more devices such as a hard drive or other non-volatile storage device 46, a read-only memory 48 (ROM 48) and a random access (and usually volatile) memory 50 (RAM 50 or operational memory 50).

The processor 40 may include an input device 52 for receiving inputs from a user or from another device. Similarly, an output device 54 may be provided within the node 41, or accessible within the apparatus 40. A network card 56 (interface card) or port 58 may be provided for connecting to outside devices, such as the network 60.

Internally, a bus 62, or plurality of buses 62, may operably interconnect the processor 42, memory devices 44, input devices 52, output devices 54, network card 56 and port 58. The bus 62 may be thought of as a data carrier. As such, the bus 62 may be embodied in numerous configurations. Wire, fiber optic line, wireless electromagnetic communications by visible light, infrared, and radio frequencies may likewise be implemented as appropriate for the bus 62 and the network 60.

Input devices 52 may include one or more physical embodiments. For example, a keyboard 64 may be used for interaction with the user, as may a mouse 66 or stylus pad 67. A touch screen 68, a telephone 69, or simply a telecommunications line 69, may be used for communication with other devices, with a user, or the like. Similarly, a scanner 70 may be used to receive graphical inputs, which may or may not be translated to other formats. The hard drive 71 or other memory device 71 may be used as an input device whether resident within the node 41 or some other node 82 (e.g. 82, 84, etc.) on the network 60, or from another network 80.

Output devices 54 may likewise include one or more physical hardware units. For example, in general, the port 58 may be used to accept inputs into and send outputs from the node 41. Nevertheless, a monitor 72 may provide outputs to a user for feedback during a process, or for assisting two-way communication between the processor 42 and a user. A printer 74, a hard drive 76, or other device may be used for outputting information as output devices 54.

In general, a network 60 to which a node 41 connects may, in turn, be connected through a router 78 to another network 80. In general, two nodes 41, 82 may be on a network 60, adjoining networks 60, 80, or maybe separated by multiple routers 78 as individual nodes 41, 82 on an internetwork.

The individual nodes 82 (e.g. 41, 78, 82, 84) may have various communication capabilities.

In certain embodiments, a minimum of logical capability may be available in any node 82. Note that any of the individual nodes 41, 78, 82, 84 may be referred to, as may all together, as a node 41 or a node 82. Each may contain a processor 42 with more or less of the other components 44–76.

A network 60 may include one or more servers 84. Servers may be used to manage, store, communicate, transfer, access, update, and the like, any practical number of files, databases, or the like for other nodes 82 on a network 60. Typically, a server 84 may be accessed by all nodes 41, 82 on a network 60. Nevertheless, other special functions, including communications, applications, directory services, and the like, may be implemented by an individual server 84 or multiple servers 84.

In general, a node 41 may need to communicate over a network 70 with a server 84, a router 78, or nodes 82. Similarly, a node 41 may need to communicate over another network (80) in an internetwork connection with some remote node 82. Likewise, individual components 42–76 may need to communicate data with one another. A communication link may exist, in general, between any pair of devices.

Figure 3:
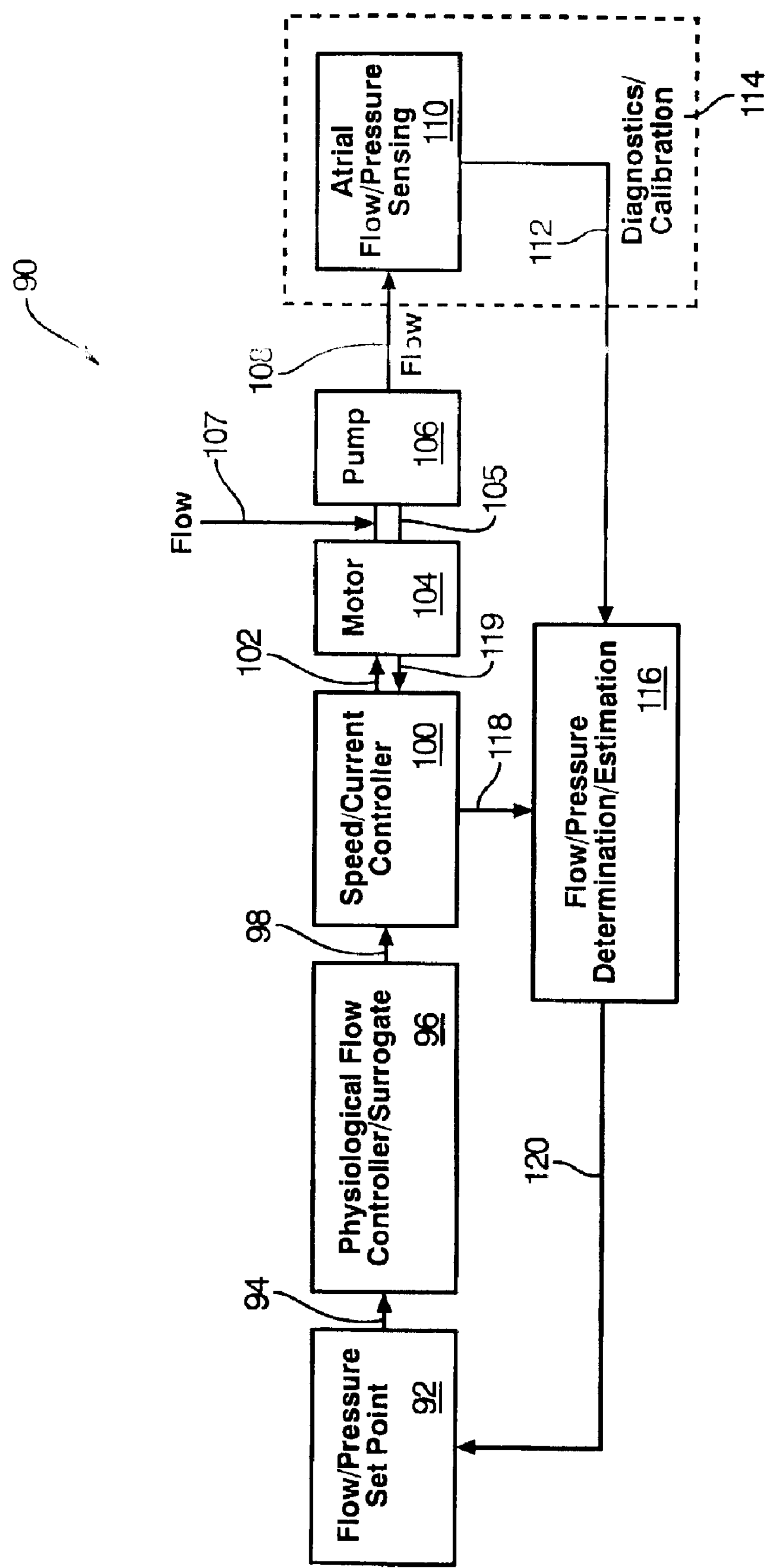
FIG. 3 is a schematic block diagram of a process for providing correlated feedback control relying on motor parameters to control physiological parameters in accordance with the invention.

Referring to FIG. 3, a method 90 for controlling a motive drive 26 in accordance with the invention, may include a variety of process steps, which may be identified separately, integrated, or otherwise modified to provide all of the required functionality, and the relationships. In general, a process 90 may include a setting 92 of a flow, pressure, or other physiological parameter at a point of desired operation, thus selecting a desired physiological state. That is, a volumetric flow rate over a period of time, assures a proper vascular delivery of nutrients, oxygen, and so forth. Thus, a volumetric flow rate may be desired, and may be used as a point for setting 92 in the process 90. Similarly, since certain physiological, and physical relationships have been developed in the medical profession in order to correspond volumetric flow rates from an aorta 22, in response to a pressure characteristic of a native ventricle 16, similar relationships may be defined for a volumetric flow rate 22 from an aorta 22, or an assist outlet 20, in response to certain parameters of a motive drive 26 or impeller 24. Indeed, correlation of the physiological relationship to such mechanical and electrical devices, is valuable and is practiced in the teachings of the present invention. Thus, in general selecting a physiological state by setting 92 a flow rate, or a pressure, desired for operation, may be a first step.

A signal 94 or output 94 from the setting step 92 may provide an input 94 to a controller 96. In general, a controller 96, may be a physiological flow controller, a surrogate therefor, or the like. That is, a controller 96 may implement a model for curve fitting in accordance with the present invention relating a desired set point 94 or setting output 94 to the operational parameters of a motor 104. Accordingly, the controller 96 may provide a map, an equation, a model, or other solution relating a physiological parameter 94 resulting from the setting 92 desired, to an input 98 required by a controller 100 for controlling the speed, current, voltage, or the like corresponding to a motor 104. Accordingly, the controller 100 provides an output 102 effective to control the motor 104. In general, a motor 104 may be a motive drive 26 of any particular type. Typically, an electric motor 104 may operate effectively. In a clinical environment, pneumatic, hydraulic, and other types of motors 104 may provide other advantages, and may be used accordingly.

In general, a pump 106 may constitute an impeller 24 in a chamber 27. Nevertheless, the motor 104 may be thought of as the motive drive 26, whereas the pump 106, may be thought of as the impeller 24 and other constituents in fluid contact with a bloodstream.

As a result of the output 102 feed by the controller 100 to the motor 104, a flow output 108 may be provided from the pump. The pump 106, is connected to operate with the motor 104 by some type of a connector 105. The connector 105 is shown as a physical shaft, schematically. Nevertheless, the connector 105 may actually be an electromagnetic field wherein the motive drive 26 or motor 104 is simply an oscillating magnetical field and the pump 106, is merely an impeller 24 operating within a chamber 27, levitated by a magnetic field, and driven by another magnetic field. Similarly, a single magnetic field may be directionally controlled in order to provide both levitation and motivation or rotation.

In general, a flow 107 of blood into a chamber 27 of a pump 106 results in a pressure increase, and a subsequent motivation of an output flow 108. The output flow 108 may be provided directly and through an assist outlet 20 to an aorta 22 (see FIG. 1). In certain embodiments, and more particularly in a clinical setting, or in a calibration mode for the method 90 or the apparatus 10, a sensing step 110 or a physiological sensor 45 may provide feedback as to the physiological response of the native heart 14 or other portion of the body of a patient in response to the output flow 108 and corresponding pressure **25*b***.

For example, in a diagnostic or calibration context, sensing 110 may include an actual measurement, either invasively, or noninvasively, corresponding to an input pressure, an output pressure, a pressure change, heart contractibility, diastolic frequency, systemic vascular resistance, a volumetric flow rate, a mass flow rate, an electromagnetic wave corresponding to a native heart, an electromagnetic wave corresponding to a nerve, a displacement of a portion of a native heart, a flow ratio between a native heart and the ventricular assist device, an occlusion measurement, a heart valve resistance, a ventricle strength, a combination of the forgoing, or the like, that may be capable of reflecting either a physiological condition, or a mechanical or electrical condition of the system 10. In certain preferred embodiments, sensing 110 may include sensing of information from both physiological sources and sensors, as well as mechanical and electrical sensors corresponding to the motor 104, pump 106, or both.

That is, physiological sensors 45 are typically not desirable in other than a clinical or calibration setting, due to their inherent invasiveness, unreliability, or both. Many times, the sensors 45 for sensing physiological conditions, may not be invasive, but may be very large, cumbersome, expensive, and the like, making them inappropriate for actual in situ operation with a patient. Or they may only be appropriate for in situ use for a short time. By contrast, the operational sensors 32 corresponding to the devices inherent in the ventricular assist device 12, such as the impeller 24, motive drive 26, and the like, are much more susceptible to miniaturization and integration directly into the ventricular assist device 12.

The output data 112 of sensing 110 may include sensing 110 of parameters corresponding to the motor 104 and pump 106, as well as the physiological condition of the patient. Accordingly, the output data 112 of sensing 110 may be provided to a determination step 116. In general, a determination step 116 may determine a physiological condition. If the output data 112 is correspondent to a physiological measurement device, such as an ultrasonic sensor, embedded or implanted flow sensor, an invasive or noninvasive pressure sensor, or the like, then the determination step 116 may actually involve calculation, calibration, measurement, and the like. On the other hand, a calibration process 114 may include actual sensing 110 and output of data 112 or a signal 112. In operation in vivo, the ventricular assist device 12 and the system 10, in general, may operate without the diagnostic system 114 or calibration portion 114 of the process 90. Instead, the determination step 116 may provide a calculated determination, some type of approximation or estimation, or the like reflecting flow, pressure, or the like through the pump 106, based on an input 118 received from the controller 100. In such an environment, the controller 100 may be responsible for providing feedback from the motor 104. For example, the controller 100 may monitor the signals 119 from the motor 104 reflecting the voltage, the electrical current, the speed, and the like, of the motor 104. In certain embodiments, the controller 100 may be able to actually measure the values, or report the values, received in the data or signal 119 from the motor 104. In other embodiments, the controller 100 may simply dictate those parameters, to the motor 104. Thus, with only the output 102 from the controller 100, an open-loop control of the motor 104 would exist. With the receipt by the controller 100 of the data 119 from the motor 104, then a closed-loop control or at least feedback monitoring by the controller of the motor 104 is possible.

Thus, in general, sensing 110 may operate to determine the actual response of the pump 106, and of the flows 105, 108 of the pump 106. Meanwhile, the determination process or step 116 determines what the flow and pressure and other operational parameters of the pump 106 and the patient are, with or without the output 112 of the sensing step 110, and with the input 118 from the controller, reflecting the condition of the motor 104.

Thus, the in vivo operation of a system 10 will have calibrated into it a process for determination 116 relying only on the inputs 118 reflecting the condition of the motor 104. Thus, the sensing 110 may be relied upon during calibration, and during clinical testing, or diagnostics, in order to provide a correlation suitable for modeling by the determination of process 116. Thus, the diagnostics portion 114 or calibration portion 114 may not be required during the in vivo operation of the ventricular assist device 12.

The determination step 116 provides an output 120 that operates as an input 120 for the setting step 92. For example, upon making a determination 116 of a flow rate condition, or a pressure condition, or other physiological state, based on either actual data 112, or based on correspondent data 118 reflecting the condition of a motor 104 or the like, the setting step 92 may then compare the data 120 of the determined condition, with the desired condition originally set. Accordingly, the set step 92 may operate as a comparator 92 providing a corrected output signal 94 to the controller 96. Accordingly, the controller 96, may proceed to generate its signal 98 to the controller 100 of the motor 104.

In modern technology, any one or more of the equations, models, implementations, numerical method approximations, curve fitting, or the like being used to correlate actual physical data 112 with a control signal 102 into the motor 104 may be implemented in one or more of the steps 92, 96, 100, 116. That is, in the illustration of FIG. 3, the functionality is described logically. Nevertheless, as a practical matter for programming, for physical integration within particular processors, and the like, any one or more of the mathematical formulations, algorithms, control equations, system solutions, or the like, may be placed in one or more process steps 92, 96, 100, 116, and may be subdivided in a suitable manner, to provide the optimal processing. Nevertheless, the logical flow of the illustration of FIG. 3 shows that certain parameters of power, of flow rate, of pressure, and the like will need to be processed in order to reflect one another. That is, voltage is not current, but has a relationship thereto. Speed, is not pressure, but may have a relationship thereto. Power consumption has a relationship to flow rate, but is not designated in the units of flow rate. Thus, in order to match liters per minute, volts, coulombs per second or amperes of current, with frequencies in cycles per second, pressures in pascals or pounds per square inch, or the like, the system of steps 92, 96, 100, 116 can operate together in order to provide an input 102 to a motor 104 to providing the necessary values of control parameters to control power, current, voltage, speed, or the like, as desired and necessary for the help of a patient supported by ventricular assist device 12 connected to a native heart 14.

Figure 4:
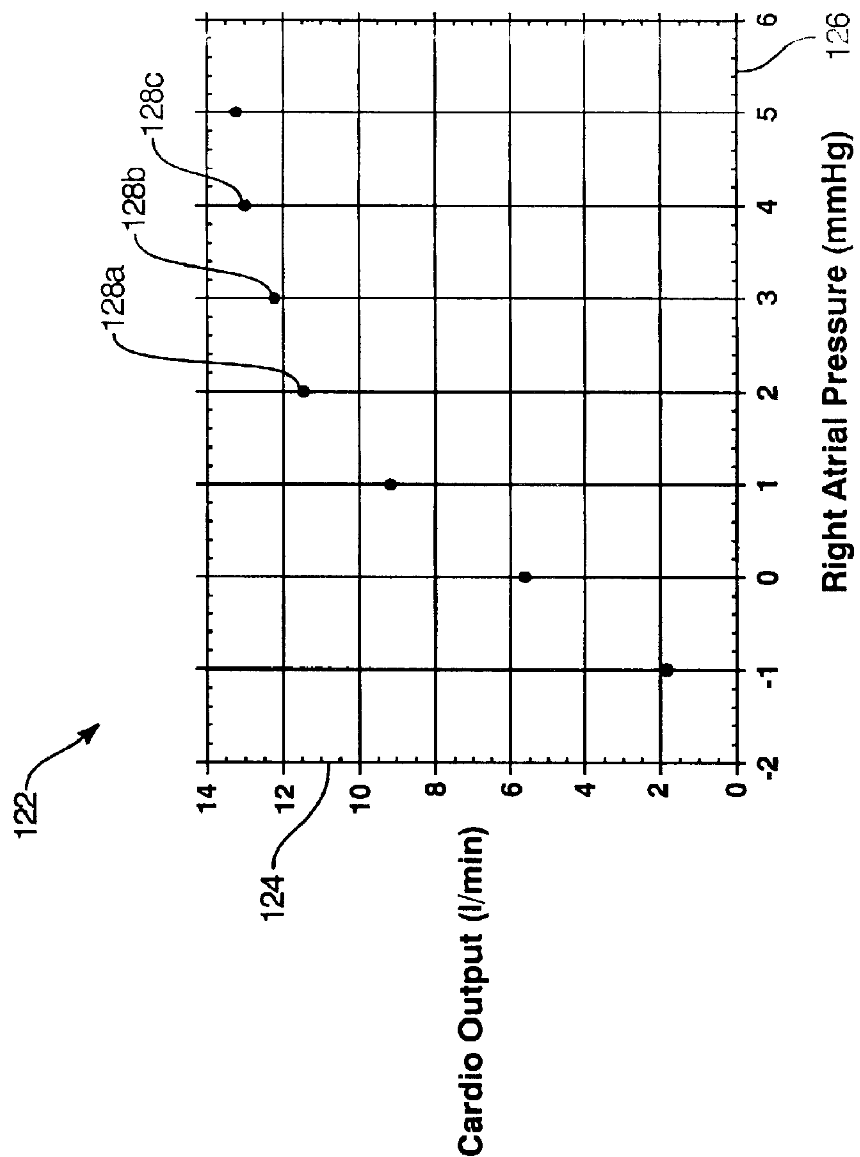
FIG. 4 is a chart illustrating a correspondence between cardiac volumetric output over time as it relates to the right atrial pressure.

Referring to FIG. 4, a chart 122 illustrates a relationship between cardiac output of blood in liters per minute on an output access 124 as a function of right atrial pressure on a domain access 126. Accordingly, various data points 128 show the rather smooth and predictable relationship between cardiac output 124 and pressure 126 in the right atrium. The relationships shown in the chart 122 may be used to create set points 94 during the setting step 92, and may be correlated to the pressure 25*b* output by the ventricular assist device 12. Thus, the Frank-Starling curve of the chart 122 may be used to create a governing equation for volumetric flow of blood over time as a result of applied pressure 126.

A similar relationship between left atrial pressure and cardiac output exists for the left side of the heart. In one embodiment, the physiological controller 96 that duplicates this relationship would return cardiac assist patients to a high level of functionality and quality of life. Even though such a system does not have the full responsiveness of the intact native circulation, it does implement much of responsiveness that a transplanted heart exhibits, which is considered to be successful for treatment of heart failure patients.

Figure 5:
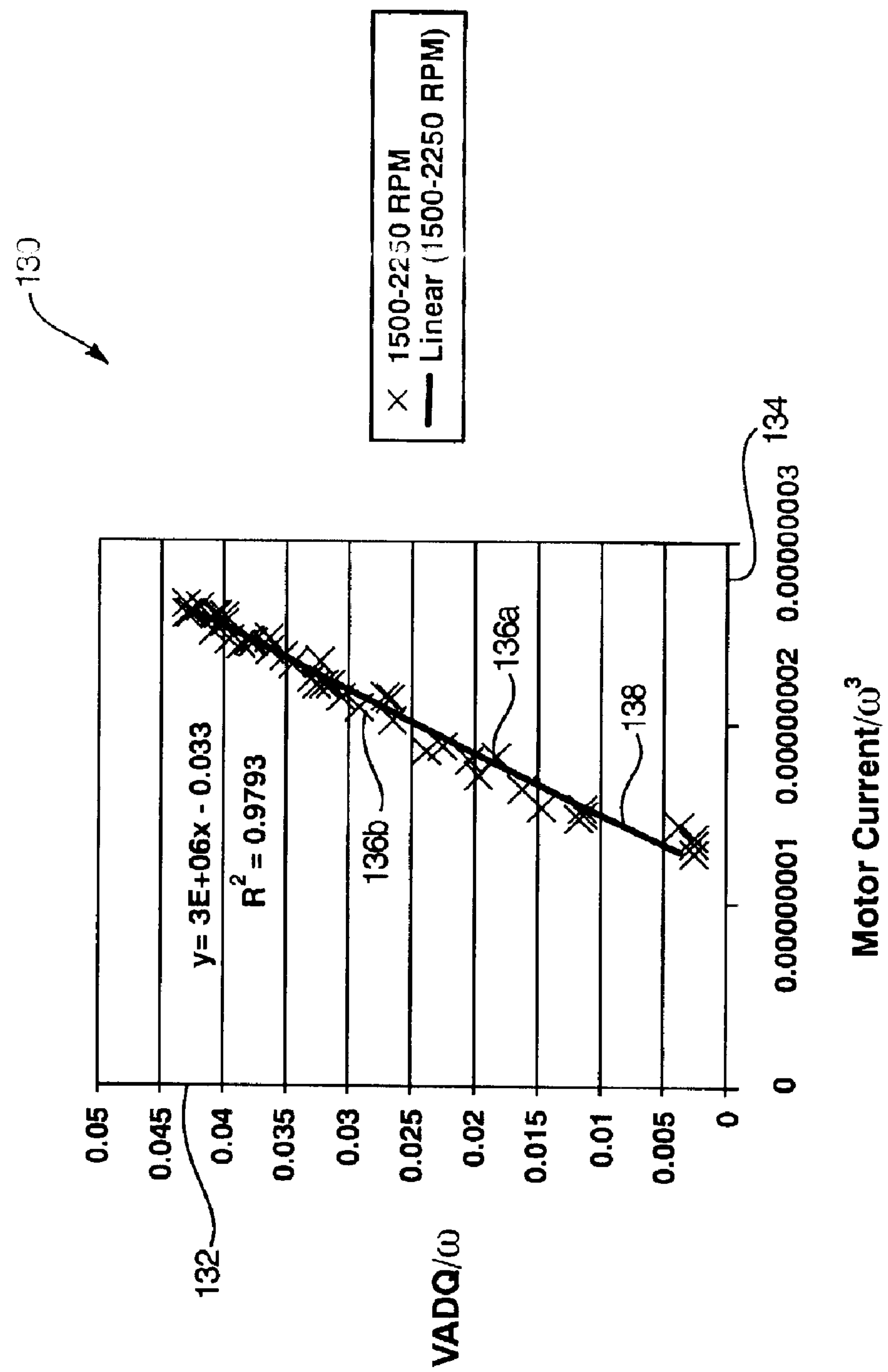
FIG. 5 is a chart illustrating one embodiment of a functional relationship between volumetric flow rate with respect to motor speed, as a function of motor current related to a power of motor speed.

Referring to FIG. 5, in one embodiment, of an apparatus and method in accordance with the invention, a chart 130 may illustrate a functional relationship determined between a unitless ratio corresponding to volumetric flow rate related to motor speed (angular velocity) as a function of the ratio of electric current into the motor, and a power of angular velocity of the motor. The operational parameters may be unitless parameters. Likewise, the physiological parameters may be unitless parameters. For example the operational or physiological parameters may be modeled such that the units of a particular parameter are cancelled out. The operation parameters may be defined independent of the physical dimensions of the blood pump.

Accordingly, the volumetric flow rate quantity 132 or range access 132 may be plotted as a function of the current variable 134 or domain access 134. One will note that the several data points 136 may be fit by one of several suitable methods to provide a more deterministic curve 138. In certain embodiments, a statistical curve fitting, including but not limited to least squares fit may be used to create the graph 138 or characteristic value 138 that forms the functional relationship between flow rate 132 and a motor current variable 134. The curve 138 is linear in this example, but may be a function of several variables or parameters, and may be a nonlinear function of those variables or parameters. Thus, for example, any suitable curve fitting method that will give reliable results and accurate representations of the data points 136 as a continuous curve 138 may be used.

It will be appreciated by those of skill in the art that there may be several specific approaches to statistical estimation theory that can be applied to practice the rotary blood pump diagnostics and control of the present invention. These approaches may include the following broad categories: 1) stochastic gradient algorithms, which include Wiener filters, 2) Kalman filters, and 3) filters that employ the method of least squares. In this context, the term filter is used in its broadest sense, i.e., a method, algorithm, piece of hardware, etc., that is employed to obtain information out of raw data.

Wiener filters are designed such that the difference between the filter output and the desired output is minimized in the "mean squared" sense. The tap weights (coefficients) for the filter are adapted over time in order to meet the minimum mean squared error criteria. Wiener filters are a member of the class of filters known as stochastic gradient algorithms. In general, Wiener filters can be implemented using transversal filter structure (known as least-mean-square algorithm), or lattice filter structure (known as gradient-lattice algorithm).

Kalman filters model and estimate the states in a state space representation of a dynamic system. A Kalman filter is similar to a Wiener filter in that statistical methods are used in the process. The actual numbers that are estimated in a Kalman filter are the states of the system that is the subject of the estimation. The behavior of the system is characterized in terms of a state space description, and the estimation is calculated in terms of the state space description. Errors in the states are measured relative to new measured information and the state values are adapted over time.

In the implementation of the Wiener or Kalman filter, assumptions are made about the statistical nature of the system being estimated. The method of least squares does not need or make assumption about the nature of the system, but uses time averaged data in the estimation routine, in essence generating its own statistics about the system.

Accordingly, the system and method of the present invention for establishing an estimation of pump flow based on statistical data may start with writing the general form of the relationship of measured pump flow to pump speed and motor current. Speed and current are two easily measured operational parameters that do not require active sensors to acquire the data.

Referring to FIG. 6, in one embodiment, a set 140 of equations may include an equation 142 characterizing a flow in terms of various ratios of current, powers of current, angular velocity, powers of angular velocity, and derivatives thereof. The selection illustrated corresponds to terms that have been found effective to characterize substantially the entire range and domain of the chart 130 of FIG. 5. In the example of FIG. 6, a series of coefficients 143 may be found by a suitable statistical analysis process to effectively form weights 143 corresponding to each term of the equation 142. Thus, the equation of 142 may be represented as the equation 144 in which flow equals a $W^T$ vector times a theta θ. Equation 146 shows that the $W^T$ vector corresponds to the vector of terms representing ratios of currents, angular velocities, powers thereof, and derivatives thereof, as the principal terms of interest. Other terms may be used. For example, other powers of current, other powers of angular velocity, high order derivatives, and the like may be used. Nevertheless, a suitable formula using the terms of equation 146 has been found effective.

Similarly, the theta vector is shown in the equation 148, and is made up of the various coefficients 143 providing the weighting factor, or contribution to each term of equation 146.

If additional terms are added to the vector $W^T$ of equation 146, then addition coefficients 143 and the vector 148 will be required. Thus, any suitable number of terms may be used in the vector 146, each having a corresponding weight 143 or coefficient 143 in the vector 148, characterizing the effect of the corresponding term.

In one embodiment, the equation 142 is based on the form of the straight line in FIG. 5 and based on the expected dynamics of the flow. The equation can be derived for the relationship between speed, current and flow, where i is motor current, ω is pump speed, and the parameters or coefficients A, B, C, D, and E 143 are unknown parameters that are to be estimated. As stated above, the parameters or coefficients A–E can be estimated in a statistical fashion based on a recursive algorithm or an algorithm that operates on a block of measured data.

For the recursive form of the statistical estimation, a matrix P is computed, and then the theta θ vector 148 is computed based on the results of an equation P(n) using the following formulas:

$$P(n) = \left[P(n-1) - \frac{P(n-1)w(n)w^T(n)P(n-1)}{\lambda + w^T(n)P(n-1)w(n)}\right]\frac{1}{\lambda}$$

$$\theta(n) = \theta(n-1) - \frac{P(n-1)w(n)\left[w^T(n)\theta(n-1) - y(n)\right]}{\lambda + w^T(n)P(n-1)w(n)}$$

where y(n) is a measurement of the actual flow through the pump, n is the present time step, and n−1 is the previous time step. This recursive approach is used to "calibrate" the θ vector 148 for the particular operating condition or state of the pump. After θ 148 is calibrated, then the flow meter is removed and the flow is now given by equation 144.

This approach allows an accurate estimation of flow, since the estimation is calibrated for each pump and motor build and for the particular operating environment. It also allows for compensation of variables or parameters such as changes in the viscosity of blood, etc.

Figure 7:
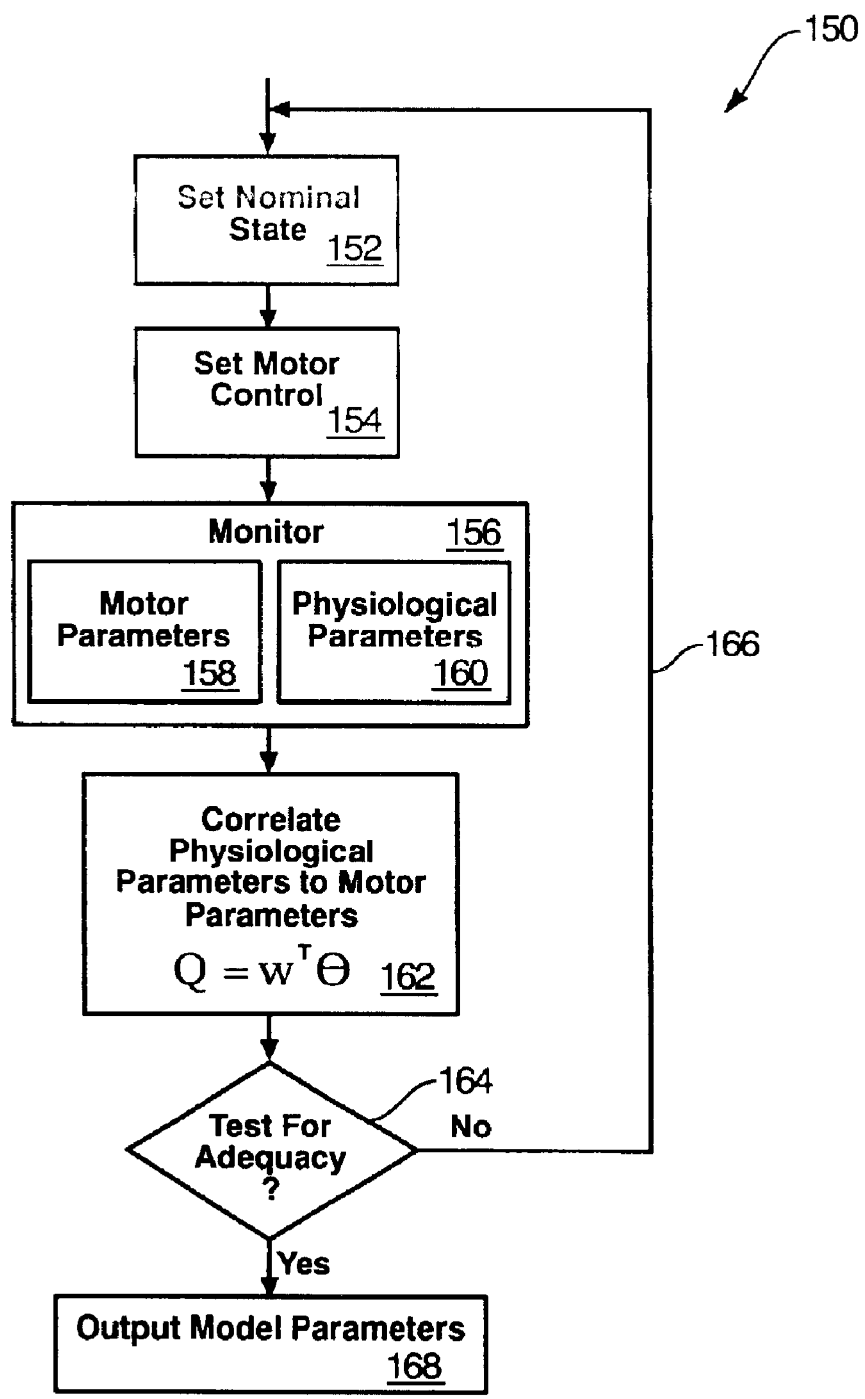
FIG. 7 is a schematic block diagram of a process for calibration of an apparatus and method in accordance with the invention.

Referring to FIG. 7, a calibration process 150 may begin with a set step 152. During the set step 152, a nominal state may established. For example, considering all of the parameters that are deemed to be worthy of accommodation within the modeling of the ventricular assist device 12, or the physiological controls or physical controls of other devices, and the like. As discussed with respect to FIGS. 1–6, a nominal state of all independent parameters may be established. Accordingly, a set step 154 may set a status on the control for the motor 104. That is, a nominal state that is set 152 for the heart 14 or for the pressures 25, or the flow rate 21, will determine based upon the modeling thereof, a set of values corresponding to motor control settings that can be utilized by th speed/current controller 100 in order to provide inputs 102 directly to the motor 104 (see FIG. 3). Likewise, the set step 152 may be thought of as providing the set point 92, and the physiological flow control modeling of the physiological controller 96. In alternative embodiments, the setting step 152 may include either the set point 94, or the controller operation 96, or both. Further, the calibration step may be part of, or include the correlation step. In one embodiment, the correlation step establishes a relationship between at least one operational parameter and at least one physiological parameter. In this embodiment, the calibration step may be thought of as the actual mapping of the at least one operation parameter to at least one physiological parameter, or vice versa.

In general, a process of monitoring 156 may include monitoring 158 the motor parameters corresponding to the motor 104, as well as monitoring 160 of the physiological parameters, corresponding to the flows 21, pressures 25, and other parameters of interest that are found measurable with respect to the native heart 14, the native ventricle 16, the aorta 22, and the like. Accordingly, monitoring 156 during a calibration process 150 could include monitoring 158 of the physical parameters of the ventricular assist device 12, as well as the physiological parameters, monitored 160 with respect to the blood flow 21, the native heart 14, and the like (see FIG. 1). In this manner, two sets of data are provided by the monitorings 158, 160, which data may be correlated. In one embodiment, the monitoring 158 may provide the outputs 118 of the process 90. Similarly, the monitoring 160 of physiological parameters may provide the outputs 112 of the sensing step 110 of the process 90.

Correlating 162 physiological parameters (e.g., information corresponding to the monitor outputs 112) with the motor parameters, physical parameters and/or other operational parameters typically corresponding to the outputs 118 or monitored data 118 corresponding to the motor 104, may be done by any suitable method. As described with respect to FIGS. 4–6, much correlation may be done statistically by a least-squares type of method. Nevertheless, higher order terms, partial differential equations, and various other types of modeling may be used in order to provide a reliable correlation 162 of flow rate as a function of the motor parameters.

A test 164 may determine adequacy of the correlation 162. For example, reliability, ability to limit outlying data points, the ability to maintain control within physiologically acceptable limits, the ability to provide motor control information that maintains a speed, current, voltage, pressure output, or the like from either the motor 104, or the pump 106 that is within the bounds of the physical realities of possible operation may be critical in some environments. In other situations, the motor 104 or pump 106 may be sufficiently robust that operational characteristics are easily able to handle any physiological limit. That is, for example, a physiological limit, or a physical device limit may exceed the bounds required for adequacy of performance of the system 10. Accordingly, a test 164 may determine whether or not the system operation is adequate. If adequacy is not achieved, then a return signal 166 or return path 166 may return to the set step 152 and adjust various values of the parameters previously established.

On the other hand, if the test 164 determines that the correlation is adequate in terms of its robust representation of reality, its ability to survive the extremes of operational values, its ability to accurately characterize and control operation of the motor 104 over a broad range of physiological parameters, or the adequacy of the ability of the mechanical and electrical systems to provide the physiological performance assistance, then the process may output 168 model parameters. In certain embodiments, the output step 168 may output the coefficients 143 that will provide the weights for the flow equation 142, 144. Additionally, the output step 168 may also provide other characterizations of the motor 104, the pump performance 106, and the like. In general, the correlation 162 may be any amount of analysis that will provide a useful relationship between one parameter that is measurable or controllable within the system 10, and another parameter that may be measurable or controllable and related thereto. Accordingly, a single equation 142, 144, or system of equations, or a solution matrix of parametric relationships, may be provided as the output 168 of model parameters. In certain embodiments, finite element methods, finite difference methods, and various types of simultaneous differential equation systems solutions, and the like may be used as the modeling, for the output 168 to feed.

Figure 8:
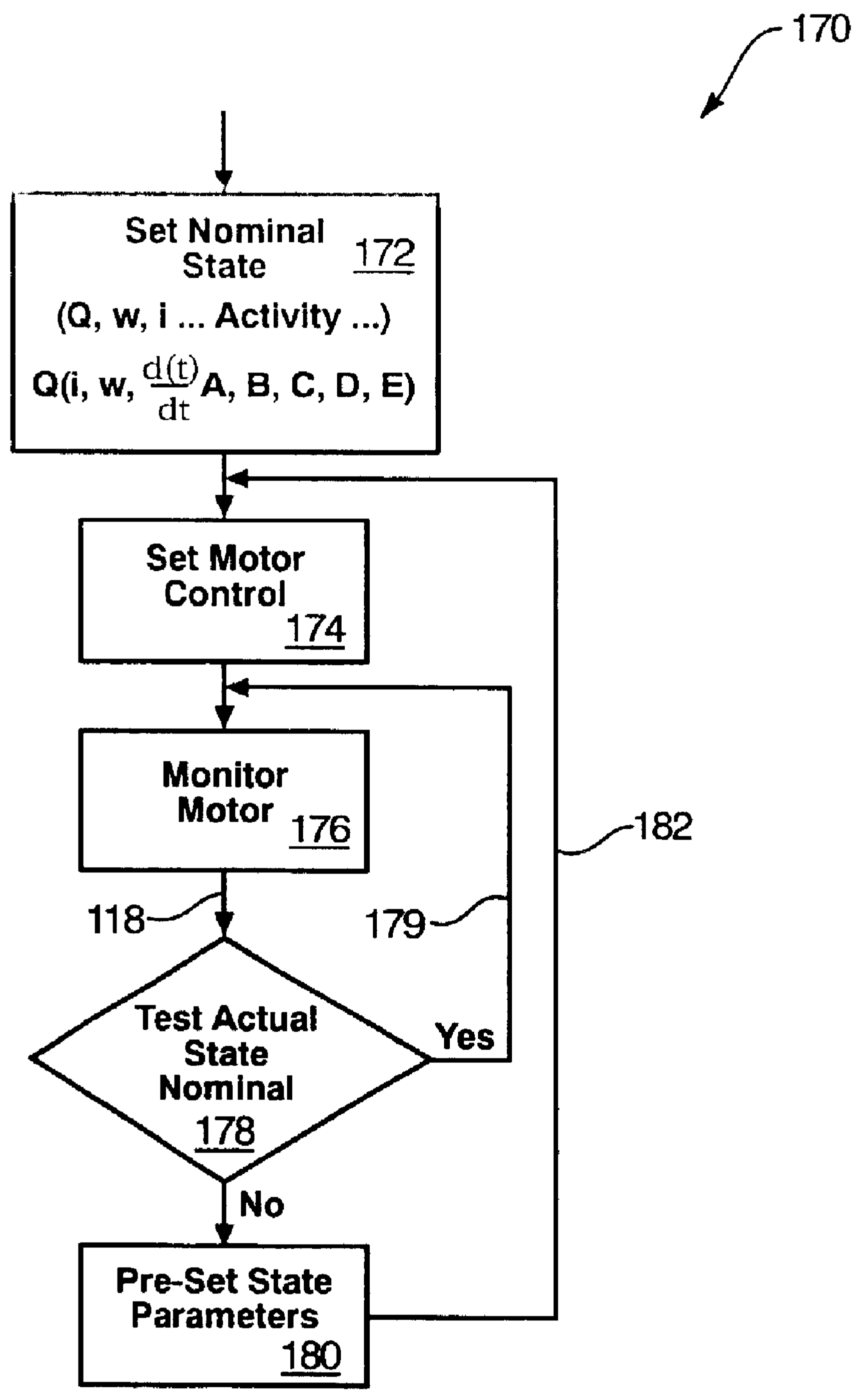
FIG. 8 is a schematic block diagram of a process of operation of a method and apparatus in accordance with the invention.

Referring to FIG. 8, an operational process 170 may begin similar to that of the calibration process 150 of FIG. 7. A set step 172 may set a nominal state for such parameters as a flow rate, an angular velocity, an electrical current, or some other activity parameter associated with the state of the system 10. In certain embodiments, the set step 172 may set a series of independent parameters including such parameters as current, angular velocity, weighting coefficients 143, derivatives of various variables or parameters such as current, speeds, power, or rations thereof, and the like. After setting 172 a nominal state for the system 10, a set step 174 may set a corresponding motor control status for the speed/current controller 100 to apply to the motor 104. The motor controls 174 reflect the correlation between the state parameters of the system 10 as set in 172, and reflect the desired state of the patient, the native heart 14, the assist inlet pressure **25*a*, the pressures and flows of the aorta 22, or any combination thereof. Accordingly, a monitor step 176 may continue to monitor the data 118 reflecting the operation of the motor 104 and pump 106 (see FIG. 3). In operation, it is possible to provide the data 112 from a sensing step 110. However, in certain embodiments, the modeling that relates the motor control setting step 174, and the state setting step 172 may obviate the need for actually monitoring of data 112 from the physiological parameters of the patient and native heart 14**.

In accordance with the output from the monitoring step 176, a test 178 may determine what the actual state is that has been estimated or determined 116 as a result of the monitoring 176. For example, the monitoring step 176 may provide outputs 118, and a test 178 may provide a comparison or determination 116 for the actual state of the physiological system (patient, native heart 14, etc.). In accordance with the output of test 178, a finding that the actual state is stable, or otherwise at a desired state, may result in a simple return 179 of the process 170 to continue monitoring 176. On the other hand, if the actual state drifts away from the desired nominal value, then a negative output to the test 178 advances the process 170 to a preset step 180. In the preset step 180, the state parameters originally set 172 at some nominal value may be changed. In certain embodiments, if the nominal state set in the set step 172 is desired to be maintained, then the state parameters may be reset 180, and the control of the process 170 may return to the set motor control step 174 for controlling the motor 104.

Figure 9:
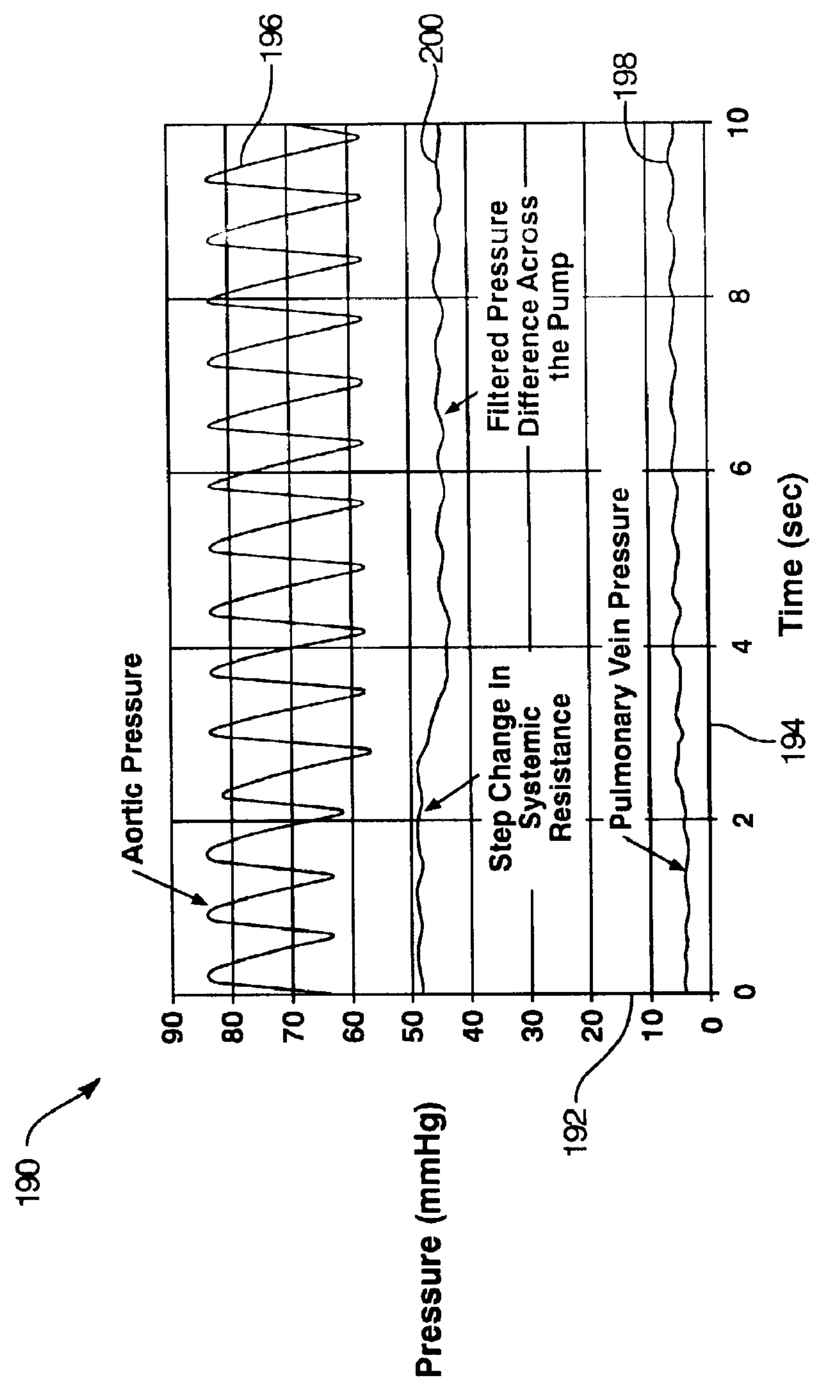
FIG. 9 is a chart illustrating a pressure across a blood pump as it corresponds to aortic pressure and pulmonary vein pressure in operation for one embodiment of an apparatus and method in accordance with the invention.

Referring to FIG. 9, in certain embodiments of an apparatus and method in accordance with the invention, physical or physiological parameters corresponding to a patient or a native heart 14 may be used to establish a modeling process for executing the control systems described with respect to FIGS. 1–8. For example, in one embodiment, a chart 190 may reflect the relationship between a vascular pressure 192, and the time 194 corresponding thereto. For example, aortic pressure 196 may correspond to a pressure that is monitored invasively or noninvasively with respect to an aorta 22. A pulmonary vein pressure 198 may be thought of as a base pressure of the cardiovascular system, with only minor cyclical variations as compared to the aortic pressure 196. That is, in general, as a result of the diastolic processes of the native heart 14 an aortic pressure 196 will be very cyclical, with large variations in amplitude. By contrast, the pulmonary vein pressure 198 corresponds to a substantially steady state of flow. Similarly, a continuous impeller 24 moving with respect to a chamber 27 under the drive of a motive drive 26, such as a motor 104, may provide an almost constant pressure and flow rate. When there is a change in system vascular resistance (SVR), this change is exhibited in the estimated pressure across the pump. SVR is one of many physiological parameters that can be obtained from accurate estimates of pump flow and pressure.

Thus, a step change in systemic resistance or systemic vascular resistance, occurring at a particular time may be accommodated by the controllers described with respect to FIGS. 1–8, in order to provide an eventual pressure difference 200 across the pump 106. The pressure difference 200, illustrated as a filtered output, and thus having less cyclical variation and amplitude swings, shows the response to the step change in systemic resistance. Thus, the resistance to flow in the vascular system, may be detected by a pressure drop across a pump 106, which may in turn be reflected in a change in the electrical current draw by the motor 104. Such physical or operational parameters of the mechanical and electrical devices of the ventricular assist device 12, may then be feed back to indicate the change in the physiological condition being supported by the native heart 14, and the ventricular assist device 12. Thus, a relationship or correlation between the operational parameters and the flow 21 of the pump 106 can be obtained for pressure across the pump 106. For example pressure across the pump can be plotted relative to motor current and nondimensionalized with respect to motor speed. The curve is obtained similar to the case in FIG. 5. The shape of the curve can be any shape that can be described by any single valued mathematical function.

Other types of input data can be used to generate the relationship or correlation similar to FIG. 5. Another example of a signal that could be used is the mechanical load on the pump bearing system. Signals available here comprise 1) magnetic bearing current or rotor position in a pump with a magnetically levitated rotor, 2) pump rotor position in a pump with a hydrodynamic bearing, 3) bearing load measured from a load cell in mechanical bearing systems.

FIG. 7 shows an example plot of aortic pressure and pulmonary vein pressure in the circulatory system. In one embodiment, SVR can be used in the feedback loop of a speed current controller 100 similar to FIG. 3. Hence, changes in SVR can be used as an indicator of required pump speed in order to supply the blood pump recipient with the proper blood flow based on their level of exertion. Other physiologic parameters can be obtained with accurate estimates of pump pressure and flow, including diastolic pressure in the patient's native ventricle. Additionally, diagnostic information regarding the possible occlusion of the soft conduits that connect the pump to blood vessels can be obtained by evaluating the estimated flow waveform. In the case of occlusion, the flow waveform demonstrates periodic dips to zero flow that can be quantified with harmonic analysis or other means.

Figure 10:
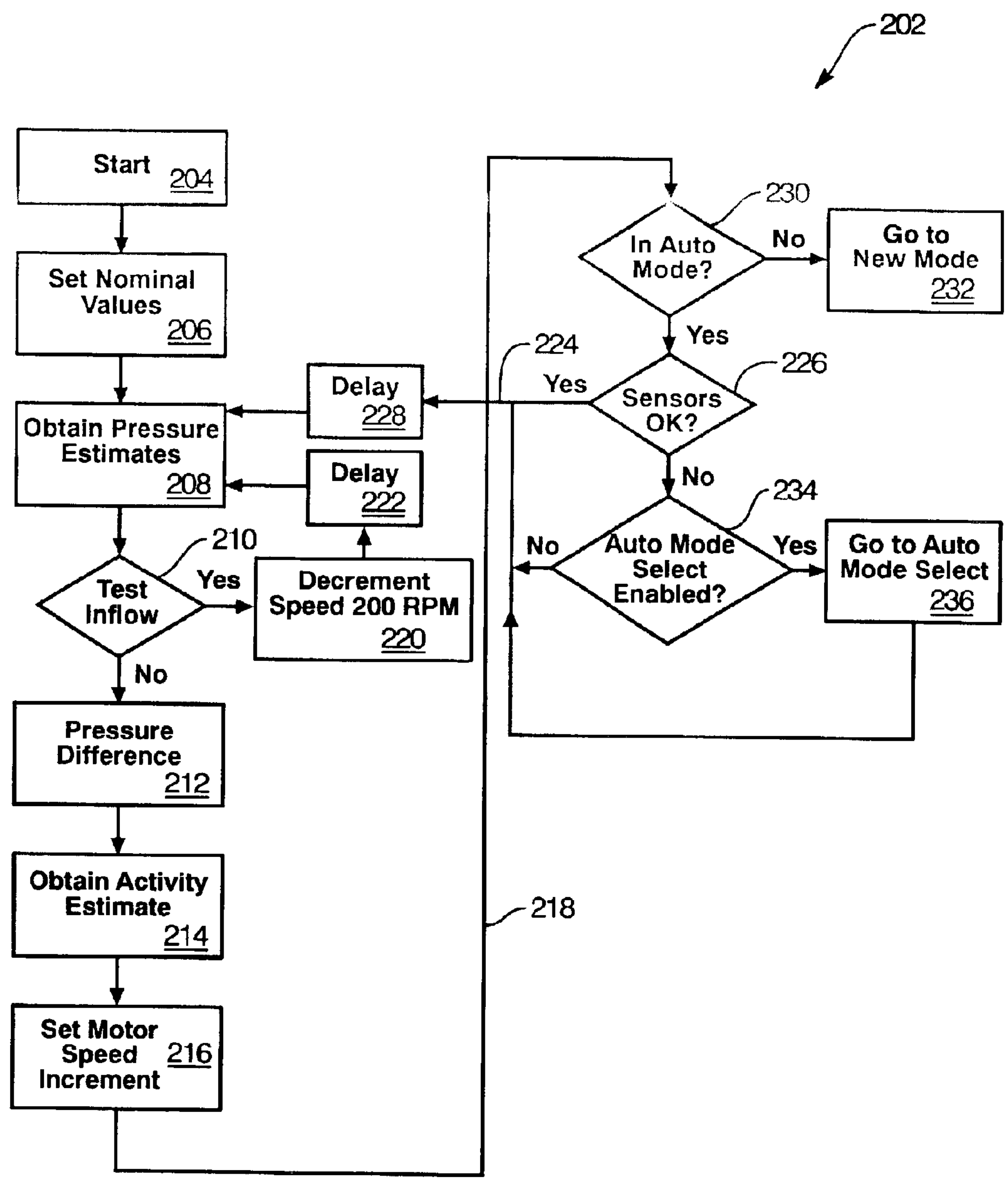
FIG. 10 illustrates a schematic block diagram of one embodiment of a process for using the information illustrated in FIG. 9.

Referring to FIG. 10, a process 202 for using the information available in the chart 190 of FIG. 9 may start 204 with a set step 206. In the set step 206, various values may be set for parameters such as a pump speed, a pressure baseline, an activity level of a user, and various other factors that may be independent from or dependent on the parameters already discussed herein above. Accordingly, an estimate step 208 may provide or obtain a pressure estimate. For example, an average over a diastolic time period at a steady state may be useful. For example, edge effects may be truncated from data, and a stable, steady state value may be used to estimate a system pressure at a system pressure 25 at an appropriate point.

Thereafter, a test 210 may determine whether or not the flow is as desired, or not. For example, an occluded flow may be reflected in the actual resistance, of the vascular system, or the load on the motor 104, or the like. In the event, that the test determines that some flow occlusion or some anomaly has occurred, then a differencing step 212 may determine a pressure difference. For example, a pressure may be subtracted from the baseline in order to provide a differential in pressure and determine whether or not it is within the correct bounds. Thereafter, an activity estimate may be estimated 214 in the process step 214 whereby the activity level can be accommodated. The activity level representation provided by the estimate 214 may then be forwarded to a set step 216 setting a motor speed increment. The motor speed increment may include any of the factors, such as speed, blending between the ventricular assist device 12, and the native heart flow 14, and the like, in order to support the estimated activity level. Thereafter, the process 202 may advance along the path 218 to other tests.

Meanwhile, should the test 210 determine that flow has been occluded, or is not as desired, then a decrement step 220 may decrement the angular velocity of the pump 104 according to some predetermined decrement. For example, in one embodiment, operating in the range of 1,500 to 2,000 revolutions per minute, a decrement of approximately ten percent may be appropriate. A value of 200 is suitable for certain embodiments. Thereafter, some sort of stability may be imposed by a delay 222, before the decrement is actually fed back into the estimation 208 from which pressure estimates are obtained.

Likewise, the estimate step 208 may also receive an input 224 from a test 226 or a test for the sensors 32, or conceivably the sensing step 110. In situ, that is in vivo, the sensor test 226 may apply only to the sensors 32 corresponding to the electrical mechanical systems 104, 106, etc. If the sensors test 226 provides an affirmative result, then a stabilizing delay step 228 may be interposed on the signal 224 before the information from the signal 224 is transmitted to the estimation step 208.

Meanwhile, a test 230 may determine whether or not the system is an automatic mode. If the system is not in an automatic mode, then a step 232 may select 232 a new mode of operation. If the process 202 is in an automatic mode 230, then the flow path 218 results in the motor speed increment being fed immediately into the automatic mode test 230, and to the sensor test 226, as illustrated.

Should the sensor test 226 result in a negative output, then a test 234 may determine whether or not the automatic mode selection has been enabled. If so, then an exit step 236 may return to the automatic mode selection process, with the stabilizing delay 228, on the signal 224. Otherwise, a negative result to the automatic mode selection test 234 may result in a direct return to the estimation process 208, by way of the signal 224 and intervening stabilizing delay 228.

A further application of the invention described here discloses an approach of estimating blood flow and contractibility of the native heart to be used in evaluating the health of the patient's native heart. A generalized equation modeling the pump and the conduits that connect the pump to the heart can be written similar to the method disclosed for estimating pump flow in FIG. 6. Temporary actual measurements are obtained that may include invasive catheters that characterize flow and pressure, or noninvasive techniques such as echocardiography to measure flow from outside the body. These measurements may be used to calibrate parameters using a filter design employing the same statistical techniques described in the flow estimation algorithm of FIG. 6. Using this approach of characterization, a continuous evaluation of the patient's native heart condition can be obtained form the blood pump date. Parameters that can be estimated include but are not limited to blood flow from the native heart, the regurgitation and function of the heart valves, contractile strength of the heart muscle, and blood pressures related to the health of the heart and circulation system.

The present invention may be embodied in other specific forms without departing from the essential characteristics thereof. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A method for monitoring a ventricular assist device, the method comprising:

measuring at least one physiological parameter reflecting a physiological state corresponding to a patient;

measuring at least one operational parameter reflecting a state of a ventricular assist device;

correlating the at least one physiological parameter with the at least one operational parameter using an estimation method; and outputting a relationship defining the at least one physiological parameter as a function of the at least one operational variable.

2. The method of claim 1, further comprising:

installing a ventricular assist device in a patient to be diagnosed;

acquiring data corresponding to the at least one operational variable of the ventricular assist device in use with the patient to be diagnosed; and predicting a value of the at least one physiological parameter for the patient to be diagnosed, based on the relationship.

3. The method of claim 1, further comprising selecting a physiological state definable by desired values of the physiological parameters and controlling input values of the operational parameters to establish the desired values of the physiological parameters.

4. The method of claim 1, wherein the estimation method comprises statistical curve fitting.

5. The method of claim 4, wherein the estimating method comprises statistical curve fitting using least squares.

6. The method of claim 4, wherein the curve fitting method is selected to provide a linear estimation.

7. The method of claim 1, wherein the estimation method comprises numerical method approximations.

8. The method of claim 1, wherein the physiological parameters are selected from an input pressure, an output pressure, a pressure change, heart contractibility, diastolic frequency, systemic vascular resistance, a volumetric flow rate, a mass flow rate, an electromagnetic wave corresponding to a native heart, an electromagnetic wave corresponding to a nerve, a displacement of a portion of a native heart, a flow ratio between a native heart and the ventricular assist device, an occlusion measurement, a physiological distress parameter, a heart valve resistance, a ventricle strength, and a combination including at least one of the forgoing.

9. The method of claim 1, wherein the operational parameters are selected from a speed, an angular velocity, an electrical current, an electrical voltage, an electrical power value, an electrical resistance, and a combination of at least one of the forgoing.

10. The method of claim 1, wherein the operational parameters are unitless parameters.

11. The method of claim 1, wherein the physiological parameters are unitless parameters.

12. The method of claim 1, further comprising the step of monitoring at least one operational parameter.

13. The method of claim 1, further comprising providing a processor.

14. The method of claim 13, further comprising using at least one operational parameter to provide diagnostic information regarding at least one physiological parameter.

15. The method of claim 1, further comprising providing an estimate of blood pressure in the ventricular assist device.

16. The method of claim 1, further comprising providing an estimate of blood flow within the ventricular assist device.

17. A method for controlling a ventricular assist device, the method comprising:

providing a ventricular assist device definable in terms of operational parameters;

providing an estimation method for correlating physiological parameters measured from a patient to at least one operational parameter;

measuring at least one physiological parameter reflecting a physiological state corresponding to a patient;

measuring at least one operational parameter reflecting a state of the ventricular assist device;

correlating physiological parameters measured from a patient to the operational parameters using an estimation method;

selecting a physiological state definable by desired values of the physiological parameters; and controlling input values of the operational parameter to establish the desired values of the physiological parameters.

18. The method of claim 7, wherein the operational parameters are selected from a speed, an angular velocity, an electrical current, an electrical voltage, an electrical power value, an electrical resistance, a bearing load, a rotor position, a magnetic bearing current, and a combination of at least one of the foregoing.

19. The method of claim 18, wherein the estimation method is calibrated using at least one operational parameter and at least one physiological parameter.

20. The method of claim 18, wherein at least one operational parameter is a unitless parameter.

21. The method of claim 18, wherein at least one physiological parameters is a unitless parameters.

22. The method of claim 18, further comprising the step of monitoring at least one operational parameter.

23. The method of claim 22, further comprising using an output from the monitoring step to control at least one operational parameter in the controlling step.

24. The method of claim 22, further comprising providing an estimate of blood pressure in the ventricular assist device.

25. The method of claim 22, further comprising providing an estimate of blood flow within the ventricular assist device.

26. The method of claim 17, wherein the physiological parameters are selected from an input pressure, an output pressure, a pressure change, heart contractility, diastolic frequency, systemic vascular resistance, a volumetric flow rate, a mass flow rate, an electromagnetic wave corresponding to a native heart, an electromagnetic wave corresponding to a nerve, a displacement of a portion of a native heart, a flow ratio between a native heart and the ventricular assist device, an occlusion measurement, a physiological distress parameter, a heart valve resistance, a ventricle strength, and a combination including at least one of the forgoing.

27. The method of claim 17, wherein the estimation method comprises statistical curve fitting.

28. The method of claim 27, wherein the statistical curve fitting comprises using a least squares equation.

29. The method of claim 27, wherein the statistical curve fitting comprises using a stochastic gradient algorithms.

30. The method of claim 29, wherein the stochastic gradient algorithm comprises a Wiener filter.

31. The method of claim 27, wherein the statistical curve fitting comprises using a Kalman filter.

32. The method of claim 27, wherein the curve fitting method is selected to provide a linear estimation.

33. The method of claim 17, wherein the estimation method comprises numerical method approximations.

34. The method of claim 17, further comprising providing a processor.

35. The method of claim 34, further comprising using at least one operational parameter to provide diagnostic information regarding at least one physiological parameter.

36. A method for controlling a ventricular assist device, the method comprising:

providing a ventricular assist device definable in terms of operational parameters;

providing an estimation method for correlating physiological parameters measured from a patient to at least one operational parameter;

measuring at least one physiological parameter reflecting a physiological state corresponding to a patient;

measuring at least one operational parameter reflecting a state of the ventricular assist device;

correlating physiological parameters measured from a patient to the operational parameters using an estimation comprising statistical curve fitting techniques;

selecting a physiological state definable by desired values of the physiological parameters;

monitoring at least one operational parameter to provide an output; and controlling input values of the operational parameter to establish the desired values of the physiological parameters using the output provided by the monitoring step.

37. An apparatus for assisting a defective heart of a patient, the apparatus comprising:

a pump;

a motive drive operably connected to drive the pump; the motive drive, further comprising an impeller for motivating blood flow from and to a native heart of a patient;

a sensor operably connected to the motive drive to detect the value of an operational parameter of the motive drive; and a processor operably connected to the motive drive and the sensor to retrieve information from the sensor, and determine a value of the operational parameter, and to provide control to the motive drive in order to affect a physiological parameter corresponding to a patient's heart, the processor programmed to use a statistical correlation between the physiological parameter and the operational parameter of the motive drive.

38. The apparatus of claim 37, wherein the operational parameter of the motive drive comprises an electrical current.

39. The apparatus of claim 37, wherein the operational parameter of the motive drive comprises a velocity.

40. The apparatus of claim 37, wherein the operational parameter of the motive drive comprises an electrical voltage.

41. The apparatus of claim 37, wherein the motive drive comprises a rotor and wherein the operational parameter of the motive drive comprises a rotor position.

42. The apparatus of claim 37, wherein the operational parameter of the motive drive comprises an magnetic bearing current.

43. The apparatus of claim 37 wherein the physiological parameter is selected from an input pressure, an output pressure, a pressure change, heart contractility, diastolic frequency, systemic vascular resistance, a volumetric flow rate, a mass flow rate, an electromagnetic wave corresponding to a native heart, an electromagnetic wave corresponding to a nerve, a displacement of a portion of a native heart, a flow ratio between a native heart and the ventricular assist device, an occlusion measurement, a physiological distress parameter, a heart valve resistance, a ventricle strength, and a combination including at least one of the forgoing.

44. The apparatus of claim 37, wherein the statistical correlation comprises approximation techniques.

45. The apparatus of claim 37, wherein the statistical correlation comprises mathematical relationship techniques.

46. The apparatus of claim 45, wherein the processor uses a statistical correlation between the physiological parameter and at least one operational parameter of the motive drive to determine a physiological state of the patient's heart.

47. The apparatus of claim 45, wherein the processor uses a statistical correlation between the physiological parameter and at least one operational parameter of the motive drive to control at least one operational parameter in order of affect a physiological parameter corresponding to a patient's heart.

* * * * *